United States Patent [19]

Fauve

[11] 4,399,124
[45] Aug. 16, 1983

[54] PEPTIDES HAVING IMMUNOSTIMULATING PROPERTIES AND PHARMACEUTICAL COMPOSITIONS CONTAINING THEM

[75] Inventor: Robert M. Fauve, Paris, France
[73] Assignee: Institut Pasteur, Paris, France
[21] Appl. No.: 268,991
[22] PCT Filed: Oct. 1, 1980
[86] PCT No.: PCT/FR80/00142
    § 371 Date: Jun. 1, 1981
    § 102(e) Date: May 28, 1981
[87] PCT Pub. No.: WO81/00847
    PCT Pub. Date: Apr. 2, 1981
[30] Foreign Application Priority Data
    Oct. 1, 1979 [FR] France .............................. 79 24448

[51] Int. Cl.$^3$ ..................... A61K 37/00; C07C 103/52
[52] U.S. Cl. ............................... 424/177; 260/112.5 R
[58] Field of Search .................. 424/177; 260/112.5 R

[56] References Cited
PUBLICATIONS

Nature, vol. 187, (1960) 773–774.
Petit, Synthetic Peptides vol. 1 (1970) 262,263.
American Chemical Society, Journal 96, (1974) 3990–3999.

Primary Examiner—Delbert R. Phillips
Attorney, Agent, or Firm—Weiser & Stapler

[57] ABSTRACT

Peptides having immunostimulating properties making them applicable to pharmaceutical compositions for the treatment or prevention of infections. They contain the sequence prolyl glycyl.

26 Claims, No Drawings

PEPTIDES HAVING IMMUNOSTIMULATING PROPERTIES AND PHARMACEUTICAL COMPOSITIONS CONTAINING THEM

The invention relates to novel peptides having biological properties, notably immunostimulating. It relates more particularly by way of novel industrial products, to peptides of samll size comprising—if one disregards the possible optical isomerism of their various aminoacyl residues—a peptide sequence (below called "common peptide sequence") in common with bradykinin and at least one aminoacyl residue separate from that to which the N-terminal end of said "common peptide sequence" is attached in the bradykinin itself. In particular, a peptide according to the invention, which comprises at the most seven aminoacyl residues, is characterised in that it contains a sequence prolyl→prolyl→glycyl, the carboxylic group of the glycyl residue being, as necessary, engaged in the peptide bond with another aminoacyl residue and in that the amino group of the first prolyl residue is engaged in a peptide bond with a different aminoacyl residue from arginyl, preferably of the lysyl or histidyl type.

The formula of bradykinin can be represented as follows:

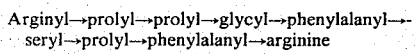

Arginyl→prolyl→prolyl→glycyl→phenylalanyl→seryl→prolyl→phenylalanyl→arginine (the direction of the arrows indicates the direction of the peptide bond: the N-terminal end towards the C-terminal end). This nomenclature will be also adopted in the following as regards the representation of the formulae of the peptides according to the invention.

Smaller peptides (among which are the pentapeptide arginyl→prolyl→prolyl→glycyl→phenyl-alanine) corresponding to sequences of bradykinin have been described in the literature. For the state of the art, reference may be made to the following documents:

Journal of the American Chemical Society, 1974, 96(12), pages 3990-9, R. J. Beuhler et al.: "Proton transfer mass spectrometry of peptides. Rapid heating technique for underivatized peptides containing arginine", Acta Phys. Chem. 1974, 20(4), pages 465-470 L. Balaspiri et al.: "Preparation of fragments of bradykinin analogs containing optically active pipecolic acid", George R. Pettit: "Synthetic peptides", Van Nostrand Reinhold Company, New York (US) pages 262, 460, NATURE, vol. 187, no. 4739, Aug. 27, 1960, Mc Millan Ltd., London (GB), E. D. Nicolaides et al.: "Synthesis and biological properties of L-Arginyl-L-Prolyl-L-Prolyl-Glycyl-L-Phenylalanyl-L-Seryl-L-Phenylalanyl-L-Arginine, an Octapeptide related to Bradykinin", pages 773-774, Canadian Journal of Physiology and Pharmacology, 1977, vol. 55, pages 855-867, D. Regoli et al.

To the extent that certain of these articles make reference to biological tests on smaller peptides than bradykinin, there has been observed, especially as regards peptides comprising at the most 7 aminoacyl residues, that they were quite devoid of the previously known activities of bradykinin. The discovery that certain of them possess important immunostimulant properties has only been more surprising.

The invention relates therefore also to pharmaceutical compositions, applicable to the treatment of diseases involving an activation mechanism of the macrophages and containing, in association with a physiologically acceptable vehicle, a peptide comprising at the most seven aminoacyl residues and including the abovesaid "common peptide sequence" whose N-terminal end is connected either to arginyl (corresponding to the aminoacyl residue contained by bradykinin at the corresponding place of its peptide chain), or to a separate aminoacyl residue.

By way of novel industrial products, the invention relates more particularly therefore to the novel peptides comprising at the most seven aminoacids and characterized in that they contain a prolyl→prolyl→glycyl sequence, the carboxylic group of the glycyl residue being, possibly, engaged in a peptide link with another aminoacyl residue, and in that the amino group of the first prolyl residue of the abovesaid prolyl→prolyl→glycyl sequence is engaged in a peptide link with a lysyl or histidyl residue.

By way of active peptides entering within the preferred pharmaceutical compositions of the invention, will be mentioned those which include at the most seven aminoacids and which contain a prolyl→prolyl→glycyl sequence, the carboxylic group of the glycyl residue being, possibly, engaged in a peptide link with another aminoacyl residue.

Advantageously these peptides contain a prolyl→prolyl→glycyl→phenylalanyl sequence.

The invention relates more particularly to those of the peptides in which the abovesaid phenylalanyl residue carries the C-terminal end of the peptide.

The invention relates more particularly again to:

by way of preferred novel industrial products, peptides such as defined above in which the amino group of the first prolyl residue of the abovesaid prolyl→prolyl→glycyl sequence is engaged in a peptide linkage with a lysyl or histidyl residue and by way of a preferred pharmaceutical compositions, those whose active principle is constituted by one of the preferred novel industrial products mentioned above or a peptide in which the amino group of the first prolyl residue of the abovesaid prolyl→prolyl→glycyl sequence is engaged in a peptide linkage with an arginyl residue.

The preferred compounds of the preceding series are constituted by pentapeptides of which the preferred representatives can be characterised by the following formulae:

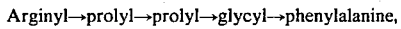

Arginyl→prolyl→prolyl→glycyl→phenylalanine,

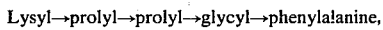

Lysyl→prolyl→prolyl→glycyl→phenylalanine,

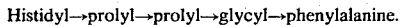

Histidyl→prolyl→prolyl→glycyl→phenylalanine.

The first of these pentapeptides is hence constituted from the same aminoacyl residues as those of the sequence of the five first aminoacids of bradykinin, whence the designation "1-5" used sometimes in the following to denote it.

The two other pentapeptides differ from the first by the nature of the first aminoacyl residue (C-terminal), the lysine for the second, histidine for the third, whence the abreviations "L5" and "H5" which will be used to denote them sometimes in the following.

And as necessary, the peptides according to the invention as defined above, include one or two additional aminoacyl residues, notably such as lysyl and/or methionyl, connected notably to the N-terminal aminoacyl residues of the abovesaid peptides through peptide linkages.

The abovesaid pentapeptides constitute the preferred active principles of the invention. They extend however also to the peptides including more aminoacyl residues. In this respect, it is interesting to mention that the derivatives of bradykinin constituted by peptides including notably the whole of the peptide sequence of bradykinin and one or two additional aminoacyl residues, such as lysyl and/or methionyl, respectively connected through peptide linkages to the N-terminal residue of bradykinin, also possess immunostimulant activity.

By way of additional preferred examples of the active principles may be mentioned:

(1) lysyl→prolyl→prolyl→glycyl→phenylalanyl→serine;
(2) lysyl→prolyl→prolyl→glycyl→phenylalanyl→seryl→proline;
(3) histidyl→prolyl→prolyl→glycyl→phenylalanyl→serine;
(4) histidyl→prolyl→prolyl→glycyl→phenylalanyl→seryl→proline;
(5) arginyl→prolyl→prolyl→glycyl→phenylalanyl→serine;
(6) arginyl→prolyl→prolyl→glycyl→phenylalanyl→seryl→proline.

The sixth and/or seventh aminoacyl residues of the abovesaid peptides can, as necessary, be replaced by one and/or two separate aminoacyl residues.

The successive amionoacyl residues of the peptides according to the invention are preferably all constituted by their levogyre isomers, with the exception of the glycyl residues which are not capable of forming dextrogyre and levogyre isomers respectively. One or several of the aminoacyl residues of the abovesaid peptides can nonetheless also be in dextrogyre form. Less biodegradable products result therefrom.

The peptides according to the invention are preferably obtained by peptide synthesis notably by the method described by R. B. Merrifield, in the article entitled "Solid Phase Peptide Synthesis. I The Synthesis of Tetrapeptide" (Synthese Peptidique en Phase Solide. I La Synthese d'un Tetrapeptide), [J. Am. Chem. Soc. 45 (1963), 2149-2154].

The invention relates also to physiologically acceptable functional derivatives of these peptides, notably the salts of acids or amines which they can form with physiologically acceptable acids or bases, or substitution derivatives of the amide or ester type, as regards the C-terminal amino acid, or derivatives of the ammonium salt or secondary amine or tertiary amine type, as regards the N-terminal amino acid.

Other features of the invention will emerge also from the description which follows of the biological properties of some of the peptides according to the invention considered by way of example.

The peptides according to the invention may be synthesized by conventional methods, for example of the type responding to the following reaction diagrams, as regards the two pentapeptides Lys-Pro-Pro-Gly-Phe and His-Pro-Pro-Gly-Phe.

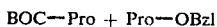
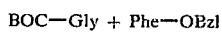

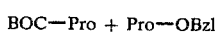
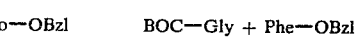

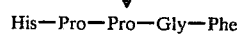

The abreviations used having the following meanings:
MA: mixed anhydrides
TFA: trifluoroacetic acid
BOC: t-butyloxycarbonyl
Z: benzyloxycarbonyl
OBzl: benzylester.

BIOLOGICAL PROPERTIES

The results obtained with the products "1-5", "L5" and "H5" are representative of those which can be established on the occasion of the application of the active principles of the invention.

I—Increase in survival of mice on infection by *Listeria monocytogenes* after treatment with the active principles of the invention Mice in lots of 10 animals received, intravenously, either only 0.5 ml of an apyrogenic solution of 0.15 M NaCl, or 0.5 ml of the same solution containing $10^{-4}$ M of said active principles. Twelve hours later, each lot was divided into two batches of five or six mice. The mice of the first batch received, intravenously, $0.2 \times 10^5$ *Listeria monocytogenes* and those of the second $0.6 \times 10^5$ *Listeria monocytogenes*.

72 hours later it was observed that the majority of treated animals survived, which manifests a considerable increase in their resistance with respect to *Listeria monocytogenes*, whereas the controls all perished.

II—Reduction in the multiplication of *Listeria monocytogenes* in the liver and the spleen of mice treated by the active principles of the invention Mice in four batches of 4 animals were treated under the same conditions as previously. Twelve hours later, the mice were all inoculated, intravenously with $0.3 \times 10^5$ *Listeria monocytogenes*.

The table below summarizes the results obtained. Again, the mice treated by the active principles show, in their spleen and especially in their liver, a number of Listeria up to 500 times smaller than in the liver of the control animals.

| Treatment of the animals | Number of Listeria monocytogenes in the spleen of mice 48 h after infection | |
|---|---|---|
| NaCl 0.15 M | $7 \times 10^7 \pm 2.4$ | |
| 1-5 | $3.1 \times 10^7 \pm 1$ | $p < 0.05$ |
| L5 | $1.8 \times 10^7 \pm 0.28$ | $p < 0.0125$ |
| H5 | $2.4 \times 10^7 \pm 1.3$ | $p < 0.05$ |

III—Acceleration of the blood purging of *Salmonella typhimurium* in mice treated with the active principles of the invention The increase in the bactericidal power of the macrophages always accompanying an increase in their ingestion capacities, it was sought to measure the latter with *Salmonella typhimurium* which necessitates for its phagocytosis, contrary to *Listeria monocytogenes*, opsonizing antibodies or a considerable stimulation of the hepatic macrophages. For this, the mice were treated under the same conditions as in the preceding experiment but were inoculated with $2 \times 10^7$ *Salmonella typhimurium* intravenously.

The results reported in the table below show that bacteremia is 5 to 10 times lower than in the control animals.

| Treatment of the animals | Number of Salmonella typhimurium per ml of blood 2 h after infection | |
|---|---|---|
| NaCl 0.15 M | $1.20 \times 10^6 \pm 0.28$ | |
| 1-5 | $3.05 \times 10^5 \pm 1.6$ | $p < 0.01$ |
| L5 | $9.35 \times 10^4 \pm 7.9$ | $p < 0.0025$ |
| H5 | $7.15 \times 10^4 \pm 0.78$ | $p < 0.0025$ |

These results show that the prior injection of the active principles results in an increase in resistance of these animals towards two very virulent bacteria for the mouse: *Listeria monocytogenes* and *Salmonella la typhimurium*.

Biological tests which have been established in the foregoing are, due to the fact of their severity and the recognized analogy with infectious mechanisms in man and mice, which can be extrapolated in man with a recognized degree of presumption as particularly significant by specialists.

IV—Increase in the resistance of mice treated by the peptides according to the invention to one of the most malignant tumors of mice: Lewis carcinoma (3LL)

This tumor is maintained in the laboratory as has been described (Fauve, R. M. and Hevin, B., Ann. Immunol. (Inst. Pasteur), 1977, 128C, 923-928). 3LL cells were cultured in Eagle medium supplemented with 15% of foetal calf serum and, after washing and resuspending in Eagle medium without serum, injected in the proportion of $10^5$ cells in a volume of 50 l into the plantar pad of C57B1/6 mice. The difference between the thickness of the paw where the tumor is developed and the contralateral paw enables the development of the tumor to be evaluated.

In all cases, the products tested were injected 24 hours after inoculation of the malignant cells and, 9 days later, after having measured the thickness of the paws, the paw bearing the tumor was amputated and, 11 days later, namely 20 days after inoculation of the tumors, the animals were autopsied and the number of metastatic pumonary nodules counted. The following table summarizes the results obtained.

| Treatment of the animals (10 mice per batch) | Development of the tumor | Number of pulmonary metastases |
|---|---|---|
| NaCl 0.15 M | $326 \pm 34$ | $5.3 \pm 2.7$ |
| 1-5 | $284 \pm 33\ p < 0.0125$ | $0.7 \pm 0.11\ p < 0.0005$ |
| L5 | $295 \pm 25\ p < 0.05$ | $3.7 \pm 2$ N.S. |
| H5 | $272 \pm 41\ p < 0.05$ | $0.5 \pm 0.10\ p < 0.0005$ |

The results obtained are considered as significant for a $p<0.05$ (Student test) (N.S. non significant). Under these conditions, it is observed that the animals so treated have an increased resistance to Lewis carcinoma.

This test represents today one of the most severe tests that there are. The Lewis carcinoma constitutes in fact the murin solid tumor considered as the most malignant among known tumors in the animal. The results indicated below show consequently a degree of presumption considered today as one of the most significant with respect to the effectiveness that one has the right to expect from these substances in higher animals and man; this presumption being here further reinforced by the fact that the regressions observed of the tumors, especially with the "1-5" and "H5" compounds, have been obtained due to administration of the active principles after inoculation of the tumors.

Experiments whose results have been reported above show that the peptides according to the invention possess non-specific immunostimulant properties, since they are, after injection in the mouse, capable of increasing their resistance to organisms as different as the very virulent bacteria for the mouse: *L. monocytogenes, S. typhimurium* and the most malignant murin tumors, of which the Lewis carcinoma is representative.

The immunostimulant effect is obtained twelve hours before the injection of the bacteria and twenty-four hours after the injection of the malignant cells.

The particularly important activity of the pentapeptides tested is noted, more particularly those in which the N-terminal aminoacyl residue is constituted by lysine and—as regards the antitumoral activity—especially histidine.

These various compounds can hence not only be used as laboratory reagents, notably as references or standards to study the presence or not of non-specific immunostimulant properties in substances studied from this angle, but again as active principles of medicaments, capable of exerting stimulation of the reticulo-endothelial system.

It is interesting, as regards more particularly the 1-5 pentapeptide, to note that the latter does not normally result in the accident of sensitization in man, since it can, in the limit, be considered as a degradation product of bradykinin in mammifers. It is all the same totally inactive with respect to the guinea pig ileon, and general devoid of all the previously known properties of bradykinin.

The peptides according to the invention can constitute the active principle of stimulant medicaments for the reticulo-endothelial system indicated notably for the treatment or prevention in man and animal of diseases bringing into play activation of the macrophages, such as infectious diseases caused by bacterial germs and, for example, infections of tuberculosis, pasterculosis, brucelloses, listeriosis type or gram negative bacteria infections or diseases caused by certain viruses such as influenza virus.

They can also be used for the treatment of diseases due to certain parasites having in the course of their cycle a phase of passage into the blood stream or lymph stream, for example paludism, bilharziosis and filariosis. They can again be used for the treatment of toxi-infections, that is to say infections due to microbial agents whose actions are not exerted only at a localized level, or even at a general level, but also to agents inducing the release of toxins capable of acting at a distance. They are applicable to the prevention of post-surgical infections of all types. Finally, their action with respect to Lewis carcinoma renders them, with a great degree of presumption, adapted to slow down the growth of cells capable of forming the solid tumors, even of ensuring their eradication.

The compositions containing such peptides may be administered intravenously, intramuscularly, or subcutaneously, in solution in pharmaceutically acceptable and sterile vehicles, such as physiological serum (saline solution or glucose serum). The quantities administered must be established by the clinician. These amounts will advantageously be measured so that the blood concentration, notably at the moment of injection if this is the route whose adoption is envisaged, reach a value of $10^{-5}$ to $10^{-3}$ molar, more particularly $0.25 \cdot 10^{-4}$ to $1.10^{-4}$ molar.

The active agents according to the invention may also be administered orally, when they are associated with pharmaceutically acceptable solid or liquid excipients. Their administration can also be envisaged by the rectal route, when they are associated with excipients suitable for this method of administration. They can also be administered externally, for example in the form of an aerosol with a suitable vehicle suitable for this mode of administration, for example, for the treatment of nasal infections.

The agents according to the invention may also be used as active principles of pommades, notably when they are applied to external cicatrising treatments. These pommades can be produced in any manner known in itself by resorting to pharmaceutical excipients for pommades, for example lanolin. The concentration of active principle in these pommades is normally comprised between 0.5 and 2% by weight.

It is self-evident that the preceding indications of doses are only for the purpose of illustrating the possibilities of using the invention and that in fact the determination of these doses will always be subject to the evaluation of the clinician.

I claim:

1. A method of stimulating macrophages in vivo in a host which comprises administering to said host an immunostimulant effective amount of a biologically active composition which comprises a biologically acceptable carrier and a peptide which is effective for stimulating macrophages in vivo having a prolyl→prolyl→glycyl sequence and a maximum of seven aminoacyl residues.

2. The method of claim 1 wherein said peptide has a prolyl→prolyl→glycyl→phenylalanyl sequence.

3. The method of claim 2 wherein the phenylalanyl residue carries the C-terminal end of said peptide.

4. The method of claim 1 wherein the amino group of the first prolyl residue of said prolyl→prolyl→glycyl sequence is linked through a peptide linkage with another aminoacyl residue.

5. The method of claim 4 wherein said aminoacyl residue is selected from the group consisting of arginyl, lysyl or histidyl.

6. The method of any one of claims 1, 2, 3, 4 or 5 in which all the aminoacyl residues of said peptide, with the exception of glycine, are levorotatory.

7. The method of claim 1 wherein the peptide is a pentapeptide selected from the group consisting of: Arginyl→prolyl→prolyl→glycyl→phenylalanine; lysyl→prolyl→prolyl→glycyl→phenylalanine; and histidyl→prolyl→prolyl→glycyl→phenylalanine.

8. The method of claim 7 wherein from 1 to 2 additional aminoacyl residues are linked to the N-terminal aminoacyl residue of said peptides, said additional aminoacyl residue being selected from the group consisting of lysyl and methionyl.

9. The method of claim 1 wherein the carboxylic acid group of the glycyl residue is linked through a peptide linkage with another aminoacyl residue.

10. An immunostimulant peptide which peptide has not more than seven amino acid residues, which peptide has the following amino acid sequence: X→prolyl→prolyl→glycyl→phenylalanyl→Y, wherein X is an amino acid residue selected from the group consisting of lysyl and histidyl, and Y is at least one amino acid residue selected from the amino acids consisting of proline and serine, but both residues not being the same, or hydroxyl.

11. The immunostimulant of claim 10 wherein the peptide is selected from the group consisting of: Lysyl→prolyl→prolyl→glycyl→phenylalanyl→serine; lysyl→prolyl→prolyl→glycyl→phenylalanyl→seryl→proline; histidyl→prolyl→prolyl→glycyl→phenylalanyl→serine; and histidyl→prolyl→prolyl→glycyl→phenylalanyl→seryl→proline.

12. The peptide of claim 10 which is a pentapeptide having the following amino acid sequence: Lysyl→prolyl→prolyl→glycyl→phenylalanyl.

13. The peptide of claim 10 which is a pentapeptide having the following amino acid sequence: Histidyl→prolyl→prolyl→glycyl→phenylalanyl.

14. The peptide of any of claims 10, 11, 12 or 13 wherein, with the exception of glycine, all the aminoacyl residues are levorotatory.

15. A composition for stimulating an immune response in a host which comprises a biologically acceptable carrier and an immunostimulant effective amount of a pharmacologically active peptide, said peptide having a maximum of seven amino acid residues, which peptide has the following acid sequence: x→prolyl→prolyl→glycyl→phenylalanyl→Y, wherein X is an amino acid residue selected from the group consisting of lysyl and histidyl, and Y is at least one amino acid residue selected from the amino acids consisting of proline and serine but both residues not being the same, or hydroxyl.

16. The composition of claim 15 wherein the peptide is selected from the group consisting of: Lysyl→prolyl→prolyl→glycyl→phenylalanyl→serine; lysyl→prolyl→prolyl→glycyl→phenylalanyl→seryl→proline; histidyl→prolyl→prolyl→glycyl→phenylalanyl→serine; and histidyl→prolyl→prolyl→glycyl→phenylalanyl→seryl→proline.

17. The composition of claim 15 wherein the peptide is a pentapeptide having the formula: Lysyl→prolyl→prolyl→glycyl→phenylalanyl.

18. The composition of claim 15 wherein the peptide is a pentapeptide having the formula: Histidyl→prolyl→prolyl→glycyl→phenylalanyl.

19. The composition of claim 17 wherein, with the exception of glycine, all the aminoacyl residues are levorotatory.

20. A method for stimulating an immunal response in a host which comprises a administering biologically acceptable carrier and an immunostimulant effective amount of a pharmacologically active peptide, said peptide having a maximum of seven amino acid residues, which peptide has the following acid sequence: X→prolyl→prolyl→glycyl→phenylalanyl→Y, wherein X is an amino acid residue selected from the group consisting of lysyl and histidyl, and Y is at least one amino acid residue selected from the amino acids consisting of proline and serine, but both residues not being the same, or hydroxyl.

21. A method of stimulating macrophages in vivo in a host which comprises administering to said host an immunostimulant effective amount of a biologically active composition which comprises a biologically acceptable carrier and a hexa or hepta peptide selected from the group consisting of: lysyl→prolyl→prolyl→glycyl→phenylalanyl→serine; lysyl→prolyl→prolyl→glycyl→phenylalanyl→seryl→proline; Histidyl→prolyl→prolyl→glycyl→phenylalanyl→serine; Histidyl→prolyl→prolyl→glycyl→phenylalanyl→seryl→proline; arginyl→prolyl→prolyl→glycyl→phenylalanyl→serine; and arginyl→prolyl→prolyl→glycyl→phenylalanyl→seryl→proline.

22. The method of claim 20 wherein all of the aminoacyl residues forming the peptide, with the exception of glycine, are levoratory.

23. The method of claim 20 wherein the administration is parenterally in an amount which ranges from about $10^{-5}$ to about $10^{-3}$ mole.

24. The method of claim 23 wherein the dosage administered ranges from $0.25 \cdot 10^{-4}$ to $1.10^{-4}$ mole.

25. The method of claim 24 wherein the administration is parenterally in an amount of from about $10^{-5}$ to about $10^{-3}$ mole.

26. The method of claim 25 wherein the dosage administered ranges from about $0.25 \cdot 10^{-4}$ to about $1.10^{-4}$ mole.

* * * * *